(12) United States Patent
Kraus, Jr. et al.

(10) Patent No.: US 7,729,740 B2
(45) Date of Patent: Jun. 1, 2010

(54) NOISE CANCELLATION IN MAGNETOENCEPHALOGRAPHY AND ELECTROENCEPHALOGRAPHY WITH ISOLATED REFERENCE SENSORS

(75) Inventors: Robert H. Kraus, Jr., Los Alamos, NM (US); Michelle A. Espy, Los Alamos, NM (US); Andrei Matlachov, Los Alamos, NM (US); Petr Volegov, Albuquerque, NM (US)

(73) Assignee: Los Alamos National Security, LLC, Los Alamos, NM (US)

(*) Notice: Subject to any disclaimer, the term of this patent is extended or adjusted under 35 U.S.C. 154(b) by 1264 days.

(21) Appl. No.: 11/096,142

(22) Filed: Mar. 31, 2005

(65) Prior Publication Data

US 2005/0234329 A1    Oct. 20, 2005

Related U.S. Application Data

(60) Provisional application No. 60/562,337, filed on Apr. 15, 2004.

(51) Int. Cl.
*A61B 5/04* (2006.01)
*A61B 5/05* (2006.01)

(52) U.S. Cl. ................................. 600/409; 600/544
(58) Field of Classification Search ............... 600/409, 600/407, 544
See application file for complete search history.

(56) References Cited

U.S. PATENT DOCUMENTS 5,008,622 A * 4/1991 Overton et al. ............ 324/248
6,462,540 B1 * 10/2002 Kandori et al. ............ 324/248
2005/0182313 A1 * 8/2005 Tucker .................... 600/409

OTHER PUBLICATIONS

R. H. Kraus, Jr., P. Volegov, K. Maharajh, M. A. Espy, A. N. Matlashov, E. R. Flynn, "Performance of a Novel SQUID-Based Superconducting Imaging-Surface Magnetoencephalography System," Physica C, vol. 368, pp. 18-23, 2002.
Cohen, D., "Magnetoencephalography: Evidence of Magnetic Fields Produced by Alpha-rhythm Currents," Science, vol. 161 (Aug. 1968) pp. 784-786.
Cohen, D., "Magnetoencephalography: Detection of the Brain's Electrical Activity with a Superconducting Magnetometer." Science, vol. 175 (Feb. 1972) pp. 664-666.
Cohen, et al., "Magnetocardiograms Taken Inside a Shielded Room with a Superconducting Point Contact Magnetometer." Appl. Phys. Lett., vol. 16 (Apr. 1972) pp. 278-280.
Brenner, et al., "Visually Evoked Magnetic Fields of the Human Brain," Science, vol. 190 (Oct. 1975) pp. 480-482.

(Continued)

*Primary Examiner*—Eric F Winakur
*Assistant Examiner*—Helene Bor
(74) *Attorney, Agent, or Firm*—Ray G. Wilson; Mark N. Fitzgerald; Juliet A. Jones

(57) ABSTRACT

An apparatus measures electromagnetic signals from a weak signal source. A plurality of primary sensors is placed in functional proximity to the weak signal source with an electromagnetic field isolation surface arranged adjacent the primary sensors and between the weak signal source and sources of ambient noise. A plurality of reference sensors is placed adjacent the electromagnetic field isolation surface and arranged between the electromagnetic isolation surface and sources of ambient noise.

9 Claims, 4 Drawing Sheets

OTHER PUBLICATIONS

Vigário, et al., "Independent Component Approach to the Analysis of EEG and MEG Recordings," IEEE Trans. Biomed. Eng., vol. 47 (May 2000) pp. 589-593.

Wubbeler, et al., "Independent Component Analysis of Noninvasively Recorded Cortical Magnetic DC-fields in Humans," IEEE Trans Biomed Eng., vol. 47 (May 2000) pp. 594-599.

Kelha, et al., "Design, Construction, and Performance of a Large-Volume Magnetic-Shield," IEEE Trans. Magn., vol. 18 (Jan. 1982) pp. 260-270.

Kraus, Jr., et al., "Source Localization Using a Novel SQUID-Based Superconducting Imaging-Surface System," Physica C, vol. 368 (Mar. 2002) pp. 18-23.

* cited by examiner

NOISE CANCELLATION IN MAGNETOENCEPHALOGRAPHY AND ELECTROENCEPHALOGRAPHY WITH ISOLATED REFERENCE SENSORS

RELATED CASES

This application claims the benefit of provisional application Ser. No. 60/562,337, filed Apr. 15, 2004.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to magnetoencephalography (MEG) and electroencephalography (EEG), and, more particularly, to noise cancellation in MEG and EEG recordings.

BACKGROUND OF THE INVENTION

Magnetoencephalography (MEG) is a noninvasive technique that measures the direct consequence of neuronal activity in the living brain. MEG measures magnetic fields that emanate from the head, unimpeded by anatomy, and by the electromagnetic "right-hand rule" are associated with electrical currents generated by the flow of ions in and around active neurons. Other functional brain imaging modalities such as fMRI, PET, and optical techniques infer brain function indirectly by measuring changes in blood flow, volume, oxygenation, etc. that are hypothesized to be associated with neuronal activity. MEG is further unique in that it, together with EEG (electroencephalography), is the only noninvasive method of measuring brain function at sub-millisecond temporal resolution or better. The physiological processes underlying the indirect measures of brain function inherently evolve at a far slower timescale.

Cohen primary reported detecting a magnetic signal originating from the human brain in 1968 using a non-superconducting sensor [1]. Shortly thereafter a RF (radio frequency) SQUID (Superconducting QUantum Interference Device) sensor was used for the first time to measure biomagnetic signals originating from the human heart [2], and the human brain [3]. The evoked-response brain activity measured with a SQUID sensor was reported by Brenner, et al., in 1975 [4]. Once it was clear that human brain activity could be observed and measured non-invasively by instruments consisting of one or a few sensors, the goal quickly shifted to precisely localizing the neuronal sources responsible for the measured magnetic activity. The position and vector characteristics of these neuronal sources can be estimated from the inverse solution of the field distribution measured outside the head.

Magnetic field distributions were originally obtained using single sensor systems that mapped fields around the head by moving the sensor in space and presenting the same stimulus to the subject at each sensor location. By the mid-1990's multiple sensors arrays covering much of the head were commercially available from companies including 4D-Neuroimaging in the US, CTF in Canada, and Neuromag in Finland, with large projects also in place in Japan. These systems consisted of 100 sensors or more spaced at various intervals over the head using various configurations. Sensor arrangement variables including gradiometric configurations, sensor spacing and other parameters have been quantitatively modeled by Flynn [5] and Mosher [6] for performance optimization. Different designs are driven by various design parameters impacting detection efficiency, cost, and target application.

Although MEG is not truly tomographic, and source reconstruction is limited by solutions of the electromagnetic inverse problem, constraints used for source localization have demonstrated reliable and accurate results. Current MEG instrumental source location accuracy reported in the literature is approximately 2 to 4 mm, depending on signal-to-noise (S/N) of the measured MEG signal, source parameters, and a variety of other parameters. Typically, 5 to 10 mm accuracy is attained in most medical applications with the latest instruments. In addition to locating the sources of neuronal activity, MEG temporal resolution is unsurpassed by any other brain imaging method.

A typical MEG experiment involves numerous successive presentations of a given stimulus or group of stimuli to a subject for which the evoked brain response is measured. An exemplary protocol would be stimulating the receptor nerves on a fingertip using a pneumatic button. The activated touch receptors transmit a signal via peripheral afferents and the spinal cord to the thalamus, which in turn transmits the signal via third-order fibers to activate a small portion of the sensory region of cerebral cortex (primary somatosensory cortex). Neurons in the cortex are arranged in columnar structures that are associated with the receptive field location and the type of stimulus.

As neurons are activated, positive ions are rapidly transported through the cell membrane into the cell (depolarization) followed by a slightly slower outflow of positive ions (repolarization). The entire process lasts approximately 3 milliseconds (msec), not including the afferent signal propagation. This phenomenon propagates along some portion of a neuron generating a concentrated ionic flow or intracellular current inside the neuron.

MEG measures the magnetic fields that are associated through Maxwell's equations with movement of charge. Although electrodes implanted in cortex near or inside of cell bodies can measure the response of individual neurons, it is impossible for current technology to observe such a signal noninvasively (i.e., from outside the skull). MEG is a viable technique because all of the neurons in a given cortical column, or set of columns, respond roughly synchronously to a single stimulus, resulting in a superposition of the fields from hundreds or thousands of activated neurons. Nonetheless, the typical MEG signal measured during evoked response experiments is very tiny, only tens to hundreds of femtotesla ($10^{-14}$ to $10^{-13}$T). MEG instruments today universally use SQUID sensors to measure these extraordinarily small magnetic fields. A state-of-the-art production SQUID will have sensitivities down to ~2 $fT/\sqrt{Hz}$ (one femtotesla, fT, is $10^{-15}$T).

The greatest challenge to measuring magnetic fields resulting from brain activity and localizing neuronal sources is the massive amount of magnetic noise in our environment. Magnetic noise in an urban setting is commonly in the range of $10^{-9}$ to $10^{-5}$T generated by AC line noise, automobiles, trains, elevators, etc. Urban magnetic noise is many orders of magnitude larger than the fields produced by the brain. A variety of techniques have been used to reduce the ambient magnetic fields for MEG measurements including: 1) locating the MEG instrument and subject in a magnetically shielded room (MSR), 2) using gradiometric magnetic field sensors coupled to SQUIDs, 3) active compensation of magnetic noise with field coils, 4) measuring or estimating the ambient noise fields and digitally subtracting the noise from sensors that are measuring brain activity, and 5) averaging MEG data from numerous stimuli. In addition to these hardware-based approaches, a broad array of additional post-processing software algorithms have been developed to reduce noise in MEG data, such as simple filters (low-pass, high-pass, band-stop, etc.), ICA [7, 8], etc.

A typical two-layer MSR will reduce noise by at least 30 dB at 0.1 Hz and 80 dB at 100 Hz for a cost of several hundred thousand US dollars. Gradiometers will further reduce noise at the cost of some reduction of brain signal. Gradiometer performance depends on numerous parameters including gradiometer design (e.g., gradiometer order and baseline), quality of fabrication, and characteristics of the noise source (e.g., physical size, proximity). Typical primary-order gradiometers reduce ambient magnetic fields from sources such as AC power lines by about 40 dB.

Active noise compensation involves measuring the noise field and using sets of large magnetic field coils relatively distant from the MEG system to cancel the noise field by superposition [9]. Such systems produce a limited set of spatial and temporal frequencies (due to the magnetic field coil size and inductance), are extremely sensitive to mechanical effects such as vibration, and are costly. A second form of active field cancellation uses the modulation and feedback coil common to most SQUID sensors to generate the noise compensation field at the SQUID pickup loop [10]. This method has greater frequency response (though still limited by processing and conversion speeds), fewer mechanical issues, and is less costly. This approach enables suppressing ambient fields with higher spatial frequencies because the background fields can be measured in close proximity to the MEG sensors and the field compensation is performed directly at the MEG sensors. The drawback is that the ambient field sensors placed close to the MEG array will be sensitive to sources in the brain; consequently, some brain signal will be cancelled along with the background. Although active noise cancellation techniques have the advantage of reducing the dynamic range of the MEG signals (typically dominated by ambient noise), any noise inherent in the background field measurement and generation of cancellation fields will be irreversibly added to the MEG signals.

Reference sensors are used by most modern MEG systems to further reduce background by measuring the ambient fields near the MEG sensor array, projecting the ambient field to the MEG sensors, and digitally subtracting the ambient field contribution to the signal measured by the MEG sensors [11, 12]. Large dynamic range analog and digital electronics are required for both background and MEG signals to avoid saturation. Such large dynamic range electronics have only become commercially available and affordable in recent years. Additionally, reference sensors must measure the background field with low noise and sufficient resolution to minimize increasing the noise floor of the MEG signals.

Simultaneous sampling of ambient and MEG fields with subsequent projection and subtraction of background from brain signals effectively removes noise up to the Nyquist limit and eliminates phase lag caused by real-time conversion, processing, and feedback inherent in all active noise cancellation approaches. In order to accurately characterize the ambient field at the primary MEG sensors, the reference sensors must be placed as close as possible to the MEG array. However, as the reference sensors approach the MEG array, they will be increasingly sensitive to magnetic fields originating in the brain. Any method that projects fields measured at the reference sensors to the primary MEG sensors and subtracts the projected values will necessarily subtract some portion of the brain signal contained in the reference sensor measurement. Consequently, there is a tradeoff between placing reference sensors as close to the MEG sensors as possible (to accurately characterize the spatial frequency of ambient fields) while minimizing the brain signal contained in the reference sensor measurement.

Other techniques have been developed using reference sensors in close proximity to the primary MEG sensors or using the MEG sensors themselves to measure the ambient background fields. These techniques invariably apply a model-based description of the noise to separate the ambient field contribution from the fields originating in the brain. Although this approach has been shown to be quite effective, it suffers from the imperfect model describing the noise and consequently does not completely remove ambient field noise from the MEG signal. It may also remove some signal originating from the brain that is not entirely orthogonal to the model description of the ambient noise sources.

Finally, averaging MEG data from multiple stimuli (data epochs) is commonly used to increase MEG signal-to-noise (S/N). Every presentation of the stimulus evokes a reproducible and nearly identical cortical response; consequently the S/N of evoked response measurements can be greatly improved by averaging the data from a large number of stimuli. In theory, this averaging reduces both ambient field noise and brain activity that is uncorrelated with the stimuli. Although the noise is reduced by roughly $1/\sqrt{N_e}$ (where $N_e$ is the number of epochs recorded and averaged), the evoked response signal begins to degrade for large numbers of stimuli. Consequently S/N does not increase indefinitely. Furthermore, averaging epochs is not possible for all functional brain studies (e.g. epilepsy) and there is increasing evidence that effects such as alterations in the dynamics of ongoing neural synchrony would be washed out by averaging multiple epochs of evoked response recordings.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, one aspect of the present invention includes apparatus for measuring electromagnetic signals from weak signal sources. A plurality of primary sensors is placed in functional proximity to the weak signal sources with an electromagnetic field isolation surface arranged in proximity to the primary sensors and between the weak signal sources and sources of ambient noise. A plurality of reference sensors is placed in proximity to the electromagnetic field isolation surface opposite the primary sensors and on the same side of the electromagnetic isolation surface as the sources of ambient noise.

Another aspect of the present invention includes a method for obtaining a noise-free signal from weak sources of electromagnetic fields. Primary sensors are placed on a first side of an electromagnetic field isolation surface and reference sensors are placed on a second side of the electromagnetic field isolation surface opposing the primary side. The primary sensors are placed in operative proximity to the weak source of electromagnetic field. A source signal is formed from an output of the primary sensors that includes a signal from the weak source of electromagnetic fields and a reference signal is formed from an output of the reference sensors comprised essentially of ambient electromagnetic noise. A correcting signal is then formed from the reference signal and subtracted from the source signal to output the noise-free signal.

BRIEF DESCRIPTION OF THE DRAWINGS

The accompanying drawings, which are incorporated in and form a part of the specification, illustrate the present invention and, together with the description, serve to explain the principles of the invention. In the drawings:

FIG. 3A is for a SQUID near the brim of the helmet and FIG. 3B is for a SQUID near the apex of the helmet.

FIG. 4A is for a SQUID near the brim of the helmet and FIG. 4B is for a SQUID near the apex of the helmet.

DETAILED DESCRIPTION

Figure 1:
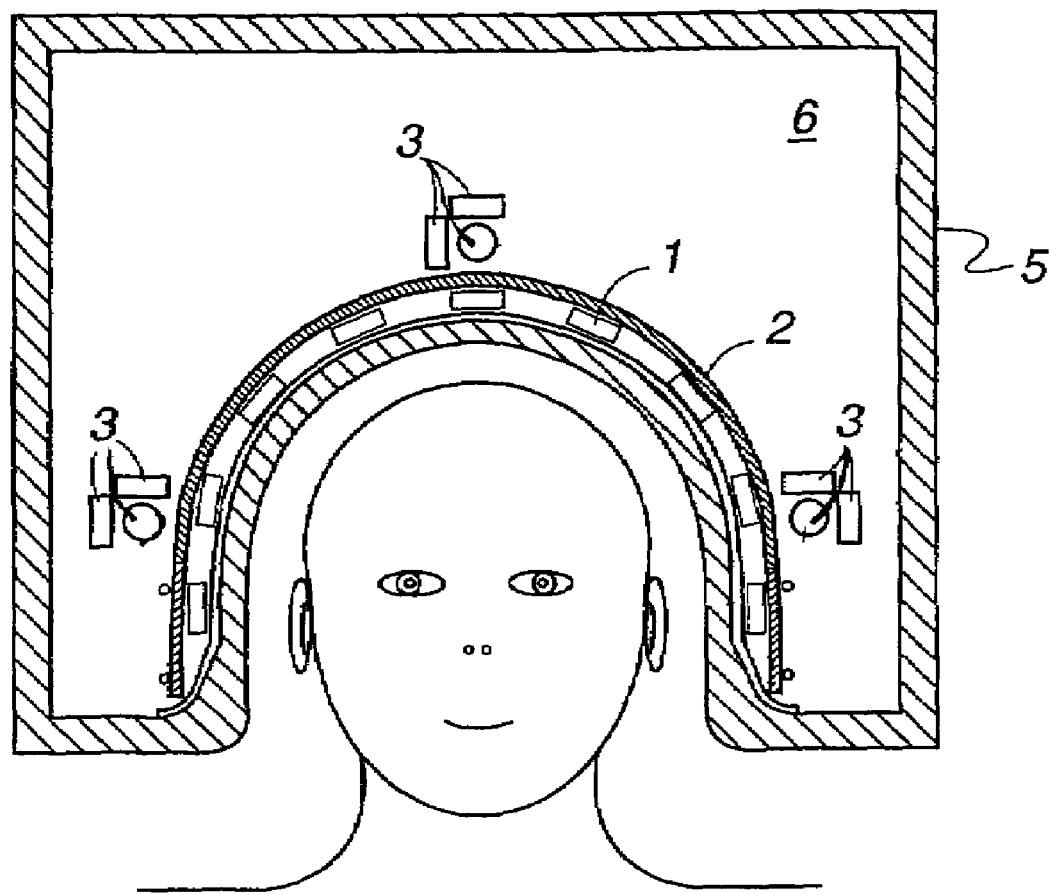
FIG. 1 is a pictorial illustration of a SIS-MEG array showing the helmet-shaped SIS surrounded by a cylindrical support and primary sensor array and exemplary reference sensors.
Figure 2:
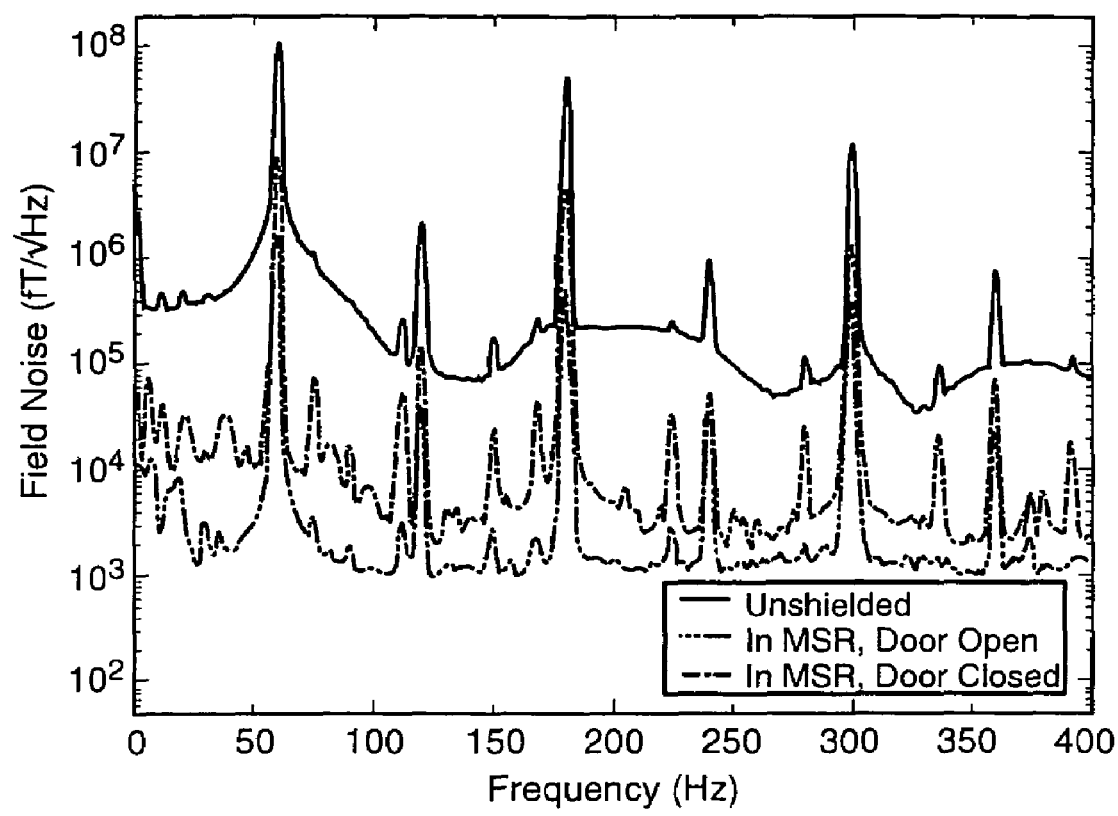
FIG. 2 graphically depicts magnetic field noise measured both inside and outside the array shown in FIG. 1.

A unique whole-head MEG system incorporating a superconducting imaging-surface (SIS) is provided with the goal of dramatically improving S/N and source localization accuracy while mitigating the extraordinary cost of current systems, as described in U.S. Pat. No. 5,008,622, issued Apr. 6, 1991, and incorporated herein by reference. A prior art Los Alamos SIS-MEG system [13, 14] consists of an array of 149 low-$T_c$ SQUID magnetometers surrounded by a superconducting helmet-like structure (fabricated with lead, a type-I superconductor below ~8K).

In addition to noise-free recording of functional brain signals with MEG, the apparatus and method of the present invention have further application to electroencephalography (EEG) recordings using SQUID sensors to measure the ambient background fields and electropotential sensors to measure brain signals. Brain function signals recorded simultaneously by MEG and EEG arrays are becoming increasingly more common because the information content in such recordings is far greater than is either alone, or even both combined but acquired separately.

While EEG is typically far less susceptible to noise than MEG, ambient environmental noise is increasingly becoming a hindrance to EEG recordings. For example, EGI (Electrical Geodesics, Inc.) has developed extremely high-density EEG electrode arrays that do not require the scalp to be "pricked" by an electrode. The contact is made directly by a conductive salt solution contained in the electrodes. While this greatly facilitates the ease of administering the dense array EEG to the subject, the electrical connection to the subject head is more resistive; consequently it is more susceptible to noise pickup. Regardless of cause, "ambient environmental" noise picked up by EEG sensors is defined as originating from electromagnetic sources outside the subject.

As used herein, the term "electromagnetic" field includes magnetic and/or electric fields arising from the brain that are measured separately or together.

The SIS system is based on the principal that Meissner currents flow in the surface of superconductors, preventing any significant penetration of magnetic fields. The original impetus behind the SIS-MEG system was to use a hemispherical SIS with a brim, or helmet, surrounding the SQUID sensor array to shield the SQUIDs from sources outside the helmet while they measure fields from nearby sources within the helmet. Sensors inside the helmet are shielded from sources outside the helmet (ambient magnetic noise) to varying degrees depending on the sensor location relative to the lower edge (brim) of the helmet. The effectiveness varies from >25 dB for sensors near the SIS brim to ~60 dB for sensors well above the brim. Unlike magnetic shielding by other non-superconducting methods (for example, MSR's) whose effectiveness drops off rapidly at low frequencies, the SIS shielding is independent of frequency.

While the original application of the SIS was to shield the SQUIDs that sense brain activity, the present invention recognizes that the SIS can be used to substantially shield reference sensors located immediately outside the helmet from brain sources, i.e., provides an isolating surface. This enables precise measurement of ambient background fields in very close proximity to the brain (primary) sensors without any contribution of signal from the sources in the brain. The SIS has the additional advantages of providing frequency independent shielding, being completely passive, and low-cost. While the SIS is a preferred way of providing an isolating surface, the use of the term "isolating surface" includes any similar device that prevents any significant penetration of magnetic fields through the surface to the reference sensors.

Localizing sources of neuronal activation from MEG measurements requires a complete description of the "forward physics" that describes how neuronal currents lead to magnetic fields at the SQUID sensors. The MEG forward model includes the complex neuronal source model that incorporates intracellular ionic currents, intercellular and extracellular volume currents, brain structure, and conductivities. The forward model for the SIS-MEG system further includes the effect of the superconducting surface on the fields generated by the primary sources. A finite element model (FEM) description of the SIS with the exact as-built geometry is used to accurately describe how the SIS impacts the forward physics of source models [15]. The FEM is used to calculate the distribution of Meissner currents in the complicated surface geometry of the SIS such that $B_\perp=0$ at the surface.

In accordance with the present invention, an additional benefit of an isolating surface is realized in conjunction with the use of reference sensors to measure the ambient magnetic fields and subtract the noise contribution to the primary MEG sensors. The SIS is used as an exemplary isolating surface here, but the use of the term "SIS" is not intended to be limiting with respect to the formation of an isolating surface.

The SIS-MEG system design, unlike any prior approach, enables the use of reference sensors to measure background fields in proximity to the isolation surface (e.g., within a few centimeters of the SIS) in close proximity to the primary sensors (e.g., within a distance that is close relative to the separation from all noise sources, typically a few centimeters) while having no measurable sensitivity to sources inside the SIS helmet. A consequence of the small spatial extent of brain sources and containment within the SIS is that reference sensors are substantially shielded (>$10^4$ reduction or >80 dB) from sources in the brain. In practice, any residual brain signal outside the SIS is well below the noise threshold of the SQUID magnetometers. The complete insensitivity of the SIS-MEG system reference sensors to brain sources is the key that enabled development of an adaptive noise cancellation (ANC) approach without concern about reducing the signal of interest or making any assumptions about the spatial character of the noise sources. An extremely important benefit is that no information about is reference sensor position is required for this approach. In addition, no model-based description of the noise or brain sources is needed to separate the contributions of the sources to the measured magnetic fields.

FIG. 1 pictorially depicts a SIS-MEG system according to one embodiment of the present invention. All elements of the system except for the reference sensor 3, for measuring ambient magnetic fields are described in the '622 patent and are only briefly described in relation to reference sensor 3. Shell 2, shown in FIG. 1, may have one or more superconducting cylindrical extensions as depicted in the '622 patent, supra, attached so that weak sources inside the shell are completely isolated from primary sensors 1 used to measure the weak magnetic fields from the sources inside the shell. Typical cryogenic dewar construction 5 is used to isolate the cryogenic shell and sensors from sources at room temperature. Superinsulation commonly used in cryogenic dewar construction, consisting of multiple layers of a highly reflective metal (such as aluminum, silver, or gold) evaporated on mylar, also serves as an RF shield to isolate sensors 1 from ambient RF noise. A vacuum is maintained between the inner and outer surfaces of the cryogenic dewar, as is common for such devices.

As constructed here, the superconducting shell 2 and all magnetic field sensors 1 and 3 are immersed in a liquid cryogen bath 6 (such as liquid helium or liquid nitrogen) that is contained within dewar 5. Cooling shell 2 and sensors 1 and 3 are required to reach the operational characteristics (superconducting state) of these type of devices.

While the approach described herein applies to any set of primary and reference magnetic field sensors, superconducting quantum interference devices, SQUIDs, as sensors 1 and 3, and a lead SIS surface as shell 2 are exemplary embodiments. As shown, each primary sensor 1 used to measure the weak magnetic field from sources of interest, and reference sensor 3 used to measure the ambient magnetic field noise, are superconducting pickup loops directly coupled to DC SQUIDs. An array of integrated SQUID primary sensors 1, e.g., 149 sensors, are spaced around the inside of the SIS in order to measure signals being generated by all regions of the brain.

In accordance with the present invention, reference sensor 3 is located about hemispherical shell 2 to detect ambient electromagnetic noise from which a correction signal is derived for the outputs of the primary sensors 1, used to measure the weak fields from the sources of interest. A suitable reference sensor 3 is similar to that used for detecting the weak fields of interest, e.g., SQUIDs. In an operating instrument, the same sensor design used to measure fields from sources of interest was used for reference sensors. However, any sensor with sufficient field sensitivity to measure magnetic field noise to the threshold of the noise floor required could be used. Examples of other possible sensors of this type include high-sensitivity magnetoresistive (GMR) type sensors, and the recently reported atomic magnetic sensors.

The shielding effect of the SIS of brain sources from reference sensors was modeled using the SIS forward physics model described in ref [13]. The shielding of brain sources from reference sensors was >85 dB for any source in a typical brain region within the SIS. This was confirmed by phantom source measurements using a precision 65-coil MEG phantom, where a lower limit of the shielding for 3 mm sources was measured to be >80 dB (frequency independent).

The configuration of reference sensors was chosen after modeling a broad array of background sources and optimizing the reference sensor positions relative to the MEG primary sensor array. It was discovered that any group of reference sensors placed with a variety of orientations in close proximity to the primary sensors that measure signals from the sources of interest would perform very well. It was also found that one could improve the performance of the noise rejection algorithm if reference sensors were able to measure the vector character of the ambient field. While noise cancellation was improved with increasing number of reference sensors, the residual noise rapidly approached the intrinsic asymptote of the sensors measuring signals from the sources of interest. Thus, the reference sensors used to demonstrate this technique were attached in groups of three sensors 3 to three orthogonal sides of a cube (not shown). The three sensors 3 on each cube sampled the three orthogonal components of the magnetic field at a given location. Five cubes (fifteen reference sensors total) were spaced around the SIS helmet: one near the apex and four spaced at approximately equal intervals around the helmet at approximately 30-degrees above the brim.

The ANC algorithm multiplies reference sensor signals by a mixing matrix and subtracts the resultant values from the MEG sensor signal. The mixing matrix is derived from the reference sensor measurement of ambient fields to determine the relative weighting of each reference sensor in computing the ambient field at each primary MEG sensor. The MEG and reference signals are defined as:

$$\{s_i(t)\}_1^n \text{—MEG channels} \qquad \text{Eqn. 1}$$

$$\{q_i(t)\}_1^m \text{—reference channels} \qquad \text{Eqn. 2}$$

Where n is the number of primary signal sensors and m is the number of reference sensors.

The corrected signal, $\tilde{s}_i$, is calculated for each channel by multiplying the reference channel signals by a mixing matrix and subtracting the product from the raw MEG signal, $s_i$, where "i" represents the 'ith' channel. This can be written in matrix notation or explicitly as:

$$\tilde{s} = s - A \cdot q \qquad \text{Eqn. 3}$$

$$s \equiv [s_i(t)]^T \qquad \text{Eqn. 4}$$

$$q \equiv [q_i(t)]^T \qquad \text{Eqn. 5}$$

$$A \equiv [a_{i,j}] \qquad \text{Eqn. 6}$$

$$\tilde{s}_i(t) = s_i(t) - \sum_{j=1}^m a_{i,j} q_j(t) \qquad \text{Eqn. 7}$$

$$i = 1 \ldots n$$

The mixing matrix, A, is computed by least square minimization of the residual in the signal after subtracting the background, which is determined by multiplying the signal-reference sensor correlation matrix by the inverse of the reference-reference correlation matrix, $C_{sq}$ and $C_{qq}^{-1}$, respectively. This simple approach can be applied to the SIS-MEG system because no brain signal is present in the reference sensors. This can be described in matrix notation by:

$$A : \min_A J\{A, s, q\} \quad \text{Eqn. 8}$$

$$J=\|\tilde{s}_i(t)\|_{l_2} \Rightarrow A=C_{sq} \cdot C_{qq}^{-1} \quad \text{Eqn. 9}$$

$$C_{sq}=[<s_i|q_k>], \ C_{qq}=[<q_k|q_j>] \quad \text{Eqn. 10}$$

$$<a|b>=\int a(t)b(t)dt \quad \text{Eqn. 11}$$

Because sources within the SIS helmet are extraordinarily well shielded from the reference sensors, A can be computed at any time during the measurement of MEG signals. Investigations have shown that A changes only modestly over the course of a protocol, typically a few tens of minutes. Finally, it should be noted that adaptive noise cancellation approach requires no information about the position of the reference sensors.

Results:

The effectiveness of the ANC method was tested in a variety of experiments with and without subjects. The SIS-MEG system was located in a single-layer MSR consisting of an aluminum eddy current shell and mu-metal static field shield. The room measured 2.7 m×2.5 m×2.5 m with a full-height door at one corner. The SIS-MEG system was located approximately in the center of the room. A plot of the ambient magnetic fields measured inside and out of the MSR is shown in FIG. 3. The effective shielding of the MSR at 60 Hz is ~40 dB. The significant noise increase at frequencies below 30 Hz inside the MSR is caused by mechanical vibrations coupling to the MSR and MEG system. This noise is dramatically reduced when building ventilation is turned off. It should be noted that the ambient magnetic noise inside the single layer MSR is similar to that measured in many unshielded environments where MEG systems are located.

The effectiveness of the ANC method implemented for the SIS-MEG system was demonstrated by comparing the raw and corrected signals for SQUID sensors near the brim and apex of the SIS helmet for cases with and without a subject in the MEG array. All SQUID channels were sampled simultaneously at 3,000 samples per second with 24-bit ADCs using 1.2 kHz anti-aliasing filters. As noted above, the passive shielding of the SIS for primary SQUID sensors near the apex of the SIS was far more effective than for those near the brim, clearly seen in FIGS. 3A and 3B, where noise in a brim SQUID is more than an order of magnitude larger than in an apical SQUID. After ANC, the de-noised SQUID signal is very similar for both brim and apical SQUID channels. This demonstrates the power of the ANC algorithm to de-noise sensor signals contaminated by noise ranging over several orders of magnitude.

Furthermore, the ANC method herein approaches the optimum de-noising attainable since the residual noise is very near the intrinsic SQUID noise of 2-3 fT/√Hz for the SQUID near the apex and only slightly higher for the brim SQUID. Only a 1 kHz anti-aliasing filter has been applied to the data shown in FIGS. 3A and 3B where 0-130 Hz of the full 0-1 kHz measured spectra is plotted to more clearly illustrate the effectiveness of the ANC method in the frequency range typically of interest for MEG measurements. The complex noise spectra below 30 Hz in both brim and apical raw data is largely due to the building ventilation unit, located approximately 10 m away, mechanically coupling to the MEG system through floor vibrations. The fact that low frequency noise is not cancelled as effectively at the brim as the apex is probably due to insufficient rigidity of the SQUID-SIS structure. The noise spectra for all apical SQUID magnetometers are indistinguishable from inherent noise spectra measured for these devices.

Figure 4A:
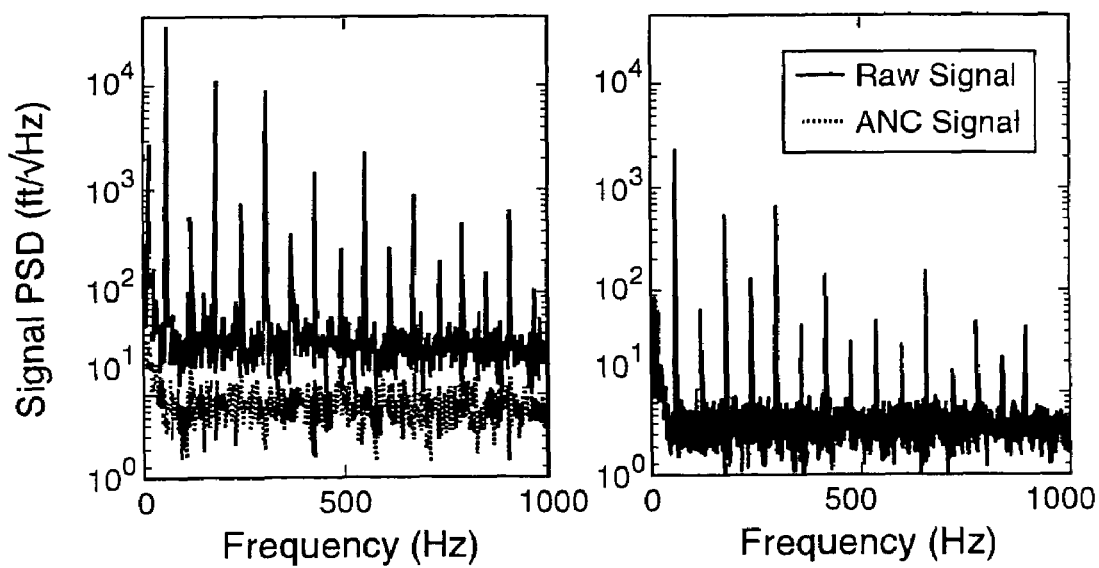
FIGS. 4A and 4B graphically depict measured ANC performance with a subject seated in the array shown in FIG. 1, where
Figure 4B:
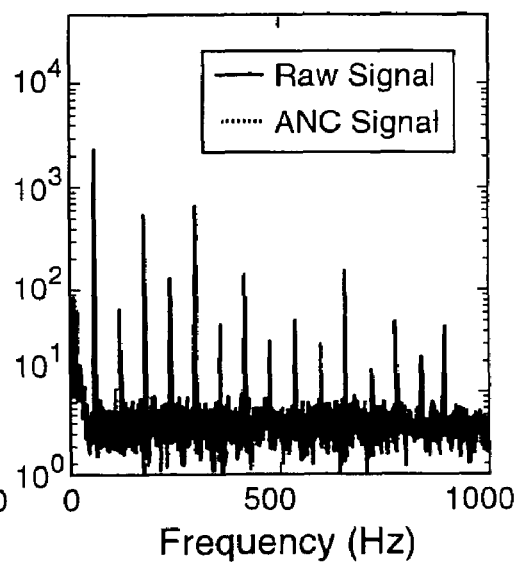

FIGS. 4A and 4B show the results of the ANC method with a subject seated under the MEG dewar immediately prior to executing an evoked response protocol. Data were acquired as described above. The full spectral results are plotted on a log scale to illustrate the effectiveness of the ANC over the full magnitude and frequency range of the signal. The ANC de-noising is as effective as without a subject and the residual noise in the apical channels is at or near the intrinsic SQUID noise and slightly larger for the brim channels. The pronounced knee at ~50 Hz in both the brim and apical de-noised spectra is caused by the uncorrelated brain activity which is not removed by the ANC.

Figure 3A:
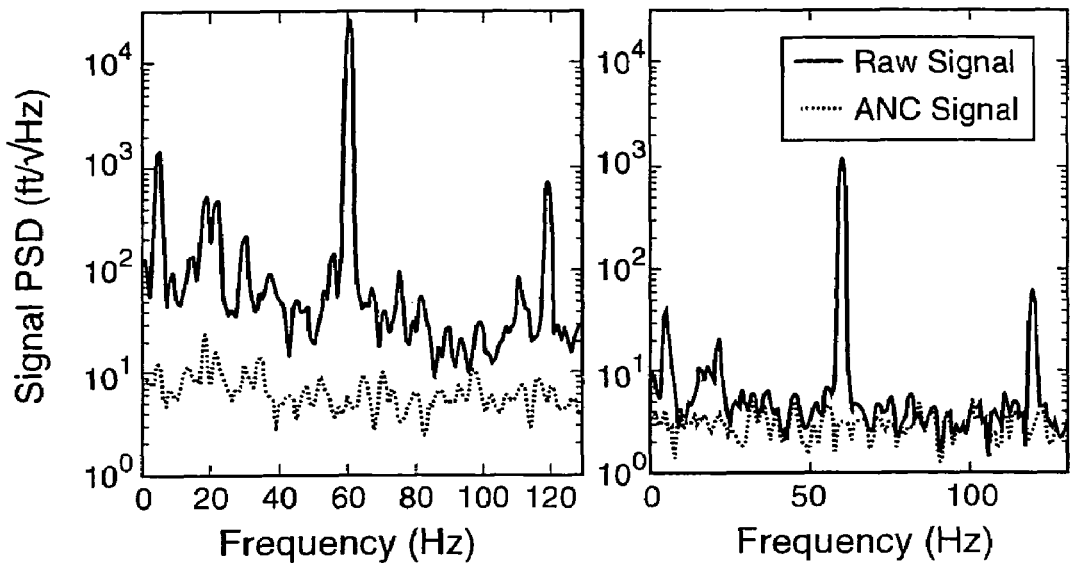
FIGS. 3A and 3B graphically depict measured adaptive noise cancellation (ANC) performance without a subject in the array shown in FIG. 1, where
Figure 3B:
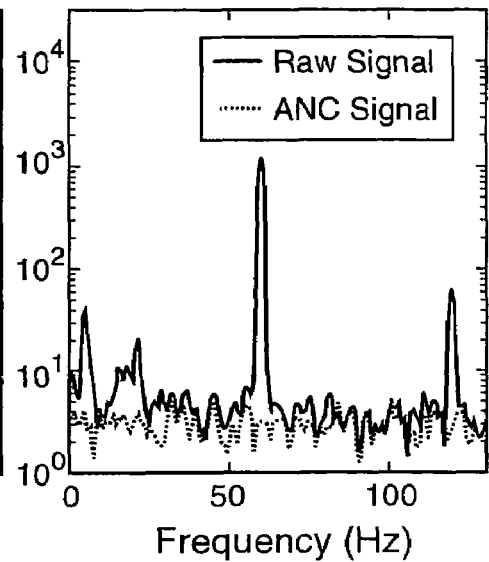
Figure 5:
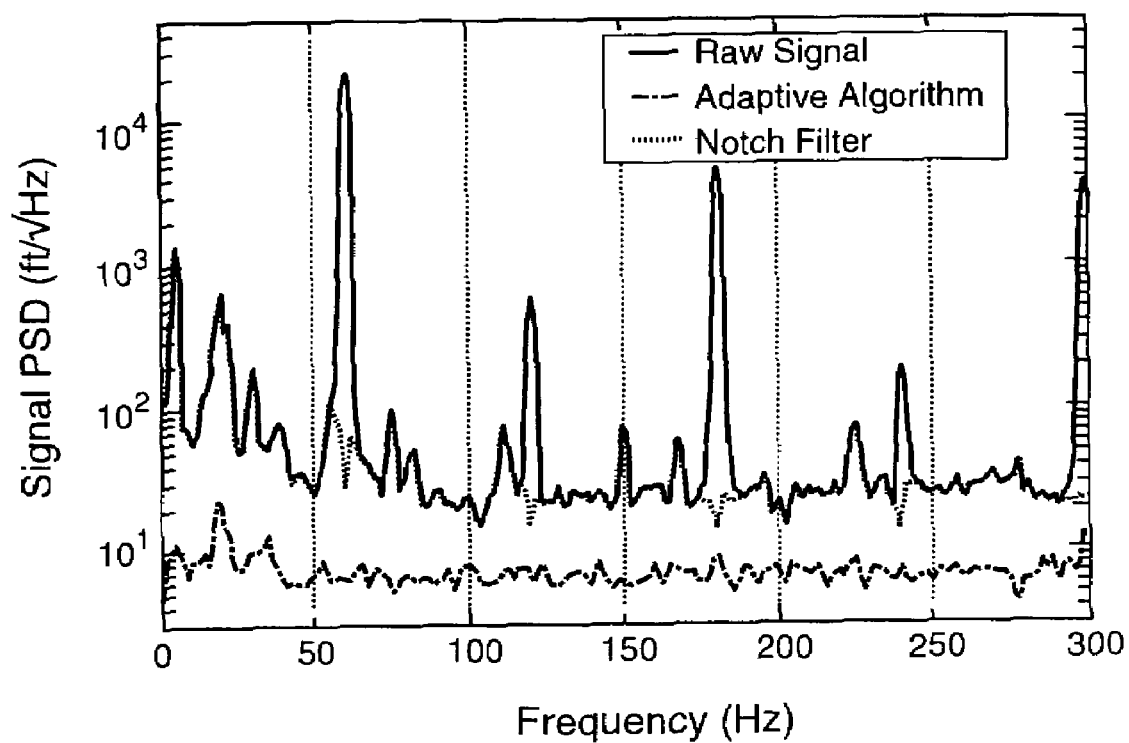
FIG. 5 graphically compares the de-noising effectiveness for the ANC method with a notch filter designed for 60 Hz and harmonics.

The huge contribution of 60 Hz line noise to the uncorrected MEG recordings could lead one to speculate that a well-crafted notch filter can effectively remove most of the noise in the spectra. A notch filter was used to remove all harmonics of 60 Hz with an absolute minimum of added artifact. A comparison of the effectiveness of applying this notch filter to the same data as shown in FIGS. 3A and 3B, with the ANC method is shown in FIG. 5. While the notch filter reduced line noise by ~50 dB, the ANC method reduced the 60 Hz line noise by nearly 70 dB. Furthermore, while the notch filter removes signals independent of any correlation with noise or brain signals, the ANC method does not remove any signal that was uncorrelated with the reference sensors. Finally, the ANC reduced noise across all frequencies upon which the notch filter had no effect. This broad-band noise is due to Johnson noise in metallic components near the SQUID array and seen primarily in the brim channels of the MEG channels.

Table 1 summarizes the effectiveness of the ANC method for various frequency bands from near DC to 150 Hz. The data in Table 1 is for the SIS-MEG system without a subject present. Although most ambient field cancellation approaches cite the "noise reduction factor" as a measure of effectiveness, the ultimate performance is for the measured noise to be that of the intrinsic SQUID noise. In fact, we have demonstrated that the ANC method herein removes substantially all ambient field contribution to the signal measured by the MEG SQUIDs. The residual noise observed in apical SQUID sensors after applying ANC is at the SQUID noise floor above 15 Hz and within a factor of two of the SQUID noise floor at lower frequencies. The residual noise in brim channels is typically a factor of two to three greater than the SQUID noise floor at higher frequencies and a factor of five for lower frequencies. In general, the largest noise reduction factors were realized where the noise is greatest, specifically at 60 Hz (power line frequency) and harmonics. Further, the largest noise in any frequency band is observed for the brim channels. We have demonstrated noise reduction factors for our ANC in excess of $10^4$ (>80 dB). The noise reduction factor appears to be limited by the magnitude of the noise available to remove and the noise floor of the SQUID.

TABLE 1

Realized noise cancellation performance for an apical MEG channel (#1) with a brim channel (#65)

| Frequency Range, Hz | PSD for ch#1 (fT/√Hz) raw | PSD for ch#1 (fT/√Hz) corrected | Noise reduction factor, ch#1 | PSD for ch#65 (fT/√Hz) raw | PSD for ch#65 (fT/√Hz) corrected | Noise reduction factor, ch#65 | Typical SQUID noise (fT/√Hz) |
|---|---|---|---|---|---|---|---|
| 2-5 | 11.8 | 6.4 | 2 | 126.6 | 26.7 | 5 | 3-4 |
| 15-25 | 18.2 | 3.3 | 6 | 787.5 | 12.3 | 64 | 2-3 |
| 59.5-60.5 | 4057.7 | 2.5 | 1600 | 73264.4 | 7.1 | >10000 | 2-3 |
| 90-100 | 1.8 | 1.4 | 1 | 27.7 | 4.9 | 5 | <2 |
| 130-15- | 1.7 | 1.4 | 1 | 26.8 | 4.5 | 5 | <2 |

The slightly higher residual noise observed in the brim SQUID sensors may be attributed to at least two causes. Primary, as noted above, the brim of the SIS structure appears to be less rigid than the apex; consequently, the observed vibration couples differently to the SQUIDs located in this region than to the reference sensors. This effect prevents optimal correlation between reference and MEG sensor measurements of the ambient field and reduces the effectiveness of the method. The fact that the reference sensors are located closer to the apex of the SIS (further from the brim) may be a second contributing factor to the less optimal performance in de-noising for the brim sensors.

ANC has proven to be exceptionally effective in all of the MEG protocols used to date. Exceptionally noise-free evoked response MEG signals were measured in an environment with 10-100 nT ambient field noise (primarily from 60 Hz power line sources). This is consistent with many unshielded environments. Although the SIS provides moderate shielding of MEG SQUID magnetometers, the most significant effect of the SIS is to shield reference sensors from the brain sources.

The application of the MEG apparatus and method described to EEG is straightforward. The reference sensors are able to measure ambient environmental noise while being completely insensitive to the brain signal. Thus, during simultaneous MEG-EEG recordings, the noise data acquired by SQUID reference sensors, as described above, can be used to remove all ambient environmental noise from the EEG sensors. This is a consequence of the complementarity of electric and magnetic parts of the electromagnetic field. Noise rejection is accomplished using the above algorithms, except that a phase term is added to either equation 1 or 2 as required by the inherent difference in character between magnetic and electric signals.

REFERENCES

Incorporated Herein by Reference for all Purposes

1. Cohen, D., "Magnetoencephalography: evidence of magnetic fields produced by alpha-rhythm currents." Science, 161 784-786 (1968)
2. Cohen, D., "Magnetoencephalography: detection of the brain's electrical activity with a superconducting magnetometer." Science 175 664-666 (1970)
3. Cohen, D., Edelsack, E. A., and Zimmerman, J. E., "Magnetocardiograms taken inside a shielded room with a superconducting point contact magnetometer." Appl. Phys. Lett. 16 278-280 (1972)
4. Brenner, D., Williamson, S. J., and Kaufman, L. "Visually evoked magnetic fields of the human brain." Science 190 480-482 (1975)
5. Flynn, E. R., "Factors which affect spatial resolving power in large array biomagnetic sensor arrays", Rev. Sci. Instr. 65, p 922
6. Mosher, J. C., Spencer, M. E., Leahy, R. M., and Lewis, P. S., 1993, "Error bounds for EEG and MEG dipole source localization", Electroenceph. and Clin. Neurophys. 86, 303-320
7. Vigário, R, Särelä, J., Jousmäki, V., Hämäläinen, M., and Oja, E., "Independent Component Approach to the Analysis of EEG and MEG Recordings," IEEE Trans. Biomed. Eng., V. 47, p. 589-593
8. Wubbeler, G; Ziehe, A; Mackert, B M; Muller, K R; Trahms, L; Curio, G., "Independent component analysis of noninvasively recorded cortical magnetic DC-fields in humans," IEEE Trans Biomed Eng., v. 47, p. 594-599 (2000)
9. Kelha, V. O.; Pikki, J. M.; Peltonen, R. S.; Penttnen, A. J.; Ilmoniemi, R. J.; Heino, J. J., "Design, Construction, and Performance of a Large-Volume Magnetic-Shield," IEEE Trans. Magn. v. 18, p. 260-270 (1982)
10. Kraus Jr., R. H., Bracht, R., Flynn, E. R., Jia, Q., Maas, P., Reagor, D., Stettler, M., "A Digital Flux-Locked Loop for High-Temperature SQUID Magnetometer and Gradiometer Systems with Field Cancellation," In Aine, C. J., Flynn, E. R., Okada, Y., Stroink, G., Swithenby, S. J., and Wood, C. C. (Eds.) Biomaq96: Advances in Biomagnetism Research, Springer-Verlag, New York, p. 63-66, (1999)
11. J. Vrba, in: H. Weinstock (Ed.), SQUID Sensors: Fundamentals, Fabrication and Applications, Kluwer, Dordrecht, 1996, pp. 117-178. Supercond. 3 (1993) 1878.
12. D. Drung, in: H. Koch, H. Lubbig (Eds.), SQUID'91, Superconducting Devices and their Applications, Springer Proceedings in Physics 64 (1991) 542.
13. Kraus, Jr., R. H., Volegov, P., Maharajh, K., Matlachov, A., Espy, M., and Flynn, E. R., "Source Localization Using a Novel SQUID-Based Superconducting Imaging-Surface System," Physica C, 368, 18-23 (2002)
14. Kraus, Jr., R. H., Matlachov, A., Volegov, P., Espy, M., Maharajh, K., and Flynn, E. R., "Source Localization Precision of the Superconducting Imaging-Surface MEG System," Biomed. Technik, 46:38 (2001)
15. Volegov, P., Kraus, Jr., R. H., Maharajh, K., Matlachov, A., Espy, M., and Flynn, E. R., "Imaging Magnetic Sources in the Presence of Superconducting Surfaces: Model & Experiment," Biomed. Technik, 46:159 (2001)

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for measuring electromagnetic signals from a weak signal source, comprising;
    a plurality of primary sensors configured to be in functional proximity to the weak signal source;
    an electromagnetic field isolation surface arranged in proximity to the primary sensors and between the weak signal source and sources of ambient noise; and
    a plurality of reference sensors in proximity to the electromagnetic field isolation surface and arranged between the electromagnetic isolation surface and sources of ambient noise,
wherein said reference sensors are substantially shielded from the weak signal source by the isolation surface, and, wherein said primary sensors, isolation surface and all reference sensors are enclosed in a single cryogenic container.

2. The apparatus of claim 1, wherein the electromagnetic field isolation surface is a superconducting surface.

3. The apparatus of claim 1, wherein the reference sensors are superconducting quantum interference devices (SQUIDs).

4. The apparatus of claim 1, wherein the primary sensors are SQUIDs.

5. The apparatus of claim 1, wherein the primary sensors are electropotential sensors.

6. A method for obtaining a noise-free signal from a weak source of electromagnetic fields comprising:
    placing primary sensors on a first side of an electromagnetic field isolation surface and reference sensors adjacent on a second side of the electromagnetic field isolation surface opposing the first side;
    placing the primary sensors in operative proximity to the weak source of electromagnetic field;
    forming a source signal from an output of the primary sensors that includes a signal from the weak source of electromagnetic fields;
    measuring a reference signal from an output of the reference sensors comprised essentially of ambient electromagnetic noise;
    forming a correcting signal from the reference signal;
    subtracting the correcting signal from the source signal to output the noise-free signal.

7. The method of claim 6, wherein the weak source of electromagnetic fields is a human brain.

8. The method of claim 7, wherein the weak source of electromagnetic fields is electrical currents generated by the flow of ions in and around active brain neurons.

9. The method of claim 6 wherein the electromagnetic field isolation surface is a superconducting imaging surface.

* * * * *